United States Patent [19]
Lupski et al.

[11] Patent Number: 5,780,223
[45] Date of Patent: Jul. 14, 1998

[54] MOLECULAR DIAGNOSIS OF AUTOSOMAL DOMINANT CHARCOT-MARIE-TOOTH DISEASE

[75] Inventors: James R. Lupski; Liu Pentao; Benjamin B. Roa; Nacer E. Abbas; Pragna I. Patel, all of Houston, Tex.

[73] Assignee: Baylor College of Medicine, Houston, Tex.

[21] Appl. No.: 129,902

[22] Filed: Sep. 30, 1993

Related U.S. Application Data

[63] Continuation-in-part of Ser. No. 879,623, May 6, 1992, abandoned, which is a continuation of Ser. No. 711,615, Jun. 6, 1991, Pat. No. 5,306,616.

[51] Int. Cl.$^6$ .............................. C12Q 1/68; C07H 21/02
[52] U.S. Cl. ............................................. 435/6; 536/23.1
[58] Field of Search .................... 435/6; 935/77, 935/78; 536/23.1, 23.2, 23.5, 24.1, 24.2

[56] References Cited

U.S. PATENT DOCUMENTS 5,306,616  4/1994  Lupski et al. ............................ 435/6

OTHER PUBLICATIONS

Reiter, L. T., et al; A recombination hotspot responsible for two inherited peripheral neuropathies is located near a mariner transposon–like element; Nature Genetics, 12:288–297; Mar. 1996.

Chance, P. F., et al; DNA Deletion Associated with Hereditary Neuropathy with Liability to Pressure Palsies; Cell; 72:143–151; Jan. 15, 1993.

Chance, P. F., et al.; Two autosomal dominant neuropathies result from reciprocal DNA duplication/deletion of a region on chromosome 17; Human Molecular Genetics; vol. 3, 2:223–228; 1994.

Chance, P. F., et al.; Two autosomal dominant neuropathies result from reciprocal DNA duplication/deletion of a region on chromosome 17; Human Molecular Genetics; vol. 3, 2:223–228; 1994.

Kiyosawa, H., et al.; Primate origin of the CMT1A–REP repeat and analysis of a putative transposon–associated recombinational hotspot; Human Molecular Genetics; vol. 5; 6:745–753; 1996.

Kiyosawa, H., et al.; Analysis of the CMT1A–REP repeat: mapping crossover breakpoints in CMT1A and HNPP; Human Molecular Genetics; vol. 4; 12:2327–2334; 1995.

LeGuern, E., et al; Constant rearrangement of the CMT1A–REP sequences in HNPP patients with a deletion in chromosome 17p11.2: a study of 30 unrelated cases; Human Molecular Genetics; vol. 4; 9:1673–1674; 1995.

LeGuern, E., et al; A de novo case of hereditary neuropathy with liability to pressure palsies (HNPP) of maternal origin: a new mechanism for deletion in 17p11.2?; Human Molecular Genetics; vol. 5; 1:103–106; 1996.

Lorenzetti, D., et al.; A 1.5–Mb Deletion in 17p11.2 p12 Is Frequently Observed in Italian Families with Hereditary Neuropathy with Liability to Pressure Palsies; Am. J. Hum. Genet. 56:91–98; 1995.

Lupski, J. R.; Editorial: DNA Diagnostics for Charcot–Marie–Tooth Disease and Related Inherited Neuropathies; Clinical Chemistry; vol. 42; 7:995–998; 1996.

Timmerman, V., et al; Molecular genetic analysis of the 17p11.2 region in patients with hereditary neuropathy with liability to pressure palsies (HNPP); Hum. Genet. 97:26–34; 1996.

Tyson, J., et al.; Deletions of Chromosome 17p11.2 in Multifocal Neuropathies; Annals of Neurology; vol. 39; 2:180–186; Feb. 1996.

Vandenberghe, A., et al.; Molecular diagnosis of Charcot–Marie–Tooth 1A disease and hereditary neuropathy with liability to pressure palsies by quantifying CMT1A–REP sequences: consequences of recombinations at variant sites on chromosome 17p11.2–12; Clinical Chemistry; 42:7 1021–1025; 1996.

Sommer et al Nucleic Acid Res 17:6749 (1989).

Sambrook et al *Molecular Cloning* 1989 pp. 6.50–6.52.

Chance et al, Cell 72:143–151 (1993).

Pentao et al, Nature Genetics 2:292–300 (1992).

*Primary Examiner*—Eggerton A. Campbell
*Attorney, Agent, or Firm*—Fulbright & Jaworski LLP

[57] ABSTRACT

A description of an isolated CMT1A-REP sequence and DNA probes to the sequence. Methods for the use of such sequences and probes to detect peripheral neuropathies. A method for detecting Charcot-Marie-Tooth disease type 1 by measuring the presence or absence of a DNA duplication in a gene locus associated with the CMT1A-REP sequence. A method for detecting Hereditary Neuropathy with Liability to Pressure Palsies by measuring the presence or absence of a DNA deletion in a gene locus associated with the CMT1A-REP sequence.

7 Claims, 16 Drawing Sheets

MOLECULAR DIAGNOSIS OF AUTOSOMAL DOMINANT CHARCOT-MARIE-TOOTH DISEASE

This application is a continuation-in-part of U. S. application Ser. No. 07/879,623 filed May 6, 1992, abandoned which is a continuation of U.S. application Ser. No. 07/711, 615 filed Jun. 6, 1991, now U.S. Pat No. 5,306,616, further claiming priority to PCT/USA2/04833, filed on Jun. 5, 1992.

The present invention was made utilizing funds of the United States Government. The United States Government is entitled to certain rights under this invention.

FIELD OF THE INVENTION

The present invention relates to the CMT1A-REP sequence, DNA probes which bind to the CMT1A-REP sequence and to methods for using the sequence and probes in the detection and diagnosis of disease in human subjects. More particularly, the present invention relates to the molecular diagnosis of the autosomal dominant Charcot-Marie-Tooth disease type 1A (CMT1A) by detection of a duplication of the gene locus and the diagnosis of hereditary neuropathy with liability to pressure palsies (HNPP) by the detection of a deletion of the gene locus.

BACKGROUND OF THE INVENTION

Charcot-Marie-Tooth disease is the most common inherited peripheral neuropathy in humans, with involvement of both motor and sensory nerves. CMT disease, characterized by gene duplication, is estimated to account for about 80% of all cases of the disease. This autosomal dominant CMT disease, exhibiting decreased nerve conductive velocity, is linked to markers from the proximal region of the short arm of chromosome 17. This form of CMT, additionally referred to herein as CMT type 1A (CMT1A), appears to be the most prevalent form of autosomal dominant CMT disease, and is characterized by the duplication of a gene locus. CMT presents in patients as variably progressive atrophy of the distal muscles of the hands and the feet. The muscular atrophy leads to an associated pes cavus foot and a claw hand deformity. The clinical signs and symptoms usually manifest by the second or third decade of life although an objective diagnosis for CMT can be made by studying electrophysiological abnormalities which are evident at a much earlier age. Most patient families demonstrate an autosomal dominant Mendelian segregation pattern, although autosomal recessive and X-linked forms of CMT have been reported. Genetically, CMT1A is inherited in an autosomal dominant fashion and is associated with a sub-microscopic duplication involving about a 1.5 megabase (Mb) of sequence on the short arm of chromosome 17.

Hereditary neuropathy with liability to pressure palsies (HNPP) is another less frequently diagnosed autosomal dominant demyelinating neuropathy that produces episodes of numbness, muscular weakness and atrophy. Motor and sensory nerve conduction velocities are sometimes mildly reduced in clinically affected patients, as well as in asymptomatic gene carriers. Pathological changes observed in peripheral nerves of HNPP patients include segmental demyelination and domaculous or "sausage-like" formations. CMT1A and HNPP are both classified as demyelinating peripheral neuropathies, however their clinical and histopathological features are distinctly different.

Present diagnostics for CMT and HNPP include electrophysiological methods to measure nerve conduction velocities, histochemistry to quantitate nerve fibers in nerve biopsy material and electron microscopy to examine the ultrastructure of involved nerves. These methods can be very expensive, painful and can cause considerable risk to the patient. The estimated cost of the complete diagnostic work-up of a patient can run greater than $5,000. The DNA based diagnostic test for CMT described in the present invention enables the physician to derive the diagnostic information from DNA isolated from peripheral blood. Obtaining the sample for a diagnosis would be at minimal discomfort, the venipuncture associated with phlebotomy, and it essentially carries no risk to the patient. This DNA based diagnostic test can be performed for less than 1/10th the cost of the present diagnostic methods. Further, the disease may be detected early at the genetic level, without need for the symptoms to be present.

SUMMARY OF THE IVVENTION

One object of the present invention is a method for diagnosing CMT1A disease.

Another object of the present invention is a method for diagnosing HNPP disease.

A further object of the present invention is the provision of a DNA probe to the CMT1A-REP sequence for diagnosing CMT1 A disease and HNPP disease.

An additional object of the present invention is the provision of an isolated CMT1A-REP sequence.

Another object of the present invention is the provision of a kit to diagnose CMT1A disease or HNPP disease.

In accomplishing some of the foregoing objects there is provided in accordance with one aspect of the present invention a method of detecting CMT1A disease in a sample containing DNA from an individual to be treated, comprising the step of measuring.in said sample the presence or absence of a DNA duplication using a probe that hybridizes to a CMT1A-REP sequence.

A further aspect of the present invention is a method detecting HNPP disease in a sample containing DNA from an individual to be tested, comprising the step of measuring in said sample the presence or absence of a DNA deletion using probes that hybridizes to a CMT1A-REP sequence.

An additional aspect of the invention includes detecting the duplication or deletion using Southern blotting analysis.

Another aspect of this invention includes detecting the duplication or deletion using pulsed field gel electrophoresis to detect specific junction fragments.

An additional aspect of the present invention is an isolated CMT1A-REP sequence and DNA probes which hybridize to the CMT1A-REP sequence.

A further aspect of the present invention is a kit for detecting CMT1A disease or for detecting HNPP disease. These kits include DNA probes which bind to the CMT1A-REP sequence.

Other and further objects and aspects will be apparent and eventually more readily understood from a reading of the following specification and by reference of the accompanying drawings forming a part thereof, wherein examples of the presently preferred embodiments of the invention are given for the purpose of the disclosure.

BRIEF DESCRIPTION OF THE FIGURES

FIG. 3A was probed with FVG11, from the proximal end of the duplication, and FIG. 3B was probed with FPL103 from the distal end. Arrows indicate the junction fragments. Both probes detect 500 kb SacII, FspI, AscI and 400 kb NotI junction fragments.

FIG. 4A is a schematic of the 17p.11.2-p.12 region. FIG. 4B–D are total human DNA, C1–1D, a parent TK-mouse cell line, and RJK88, a parent HPRT-hamster cell line. Lanes 4–9 are hybrids retaining various portions of chromosome 17. These were digested with EcoRI (Fib. 4B) or MspI (FIG. 4C and D) and hybridized to FPL14 (FIG. 4B), VAW411 (FIG. 4C), and FPL5 (FIG. 4D). Lane 1, 5.5 ug human DNA; lanes 2–9, 15 ug C1–1D, RJK88, MH22-6, 254-1D, 357-2D, 484-2D, 88H5, and LS-1, respectively. The VAW411 probe detects a 10.5 kb/6.1 kb MspI polymorphism. Hybrid lanes are identified by schematic idiograms showing the portions of chromosome 17p retained. Adjacent to the 17p idiogram are depicted the regions involved in the CMT1A duplication and the Smith-Magenis syndrome microdeletion critical region.

Hybridization of the CMT1A-REP sequence detects two novel SacII fragments in a de novo HNPP deletion patient. Two fragments (820, 770-kb) result from differential methylation of SacII sites in the proximal region of the CMT1A duplication monomer.

Figure 12:
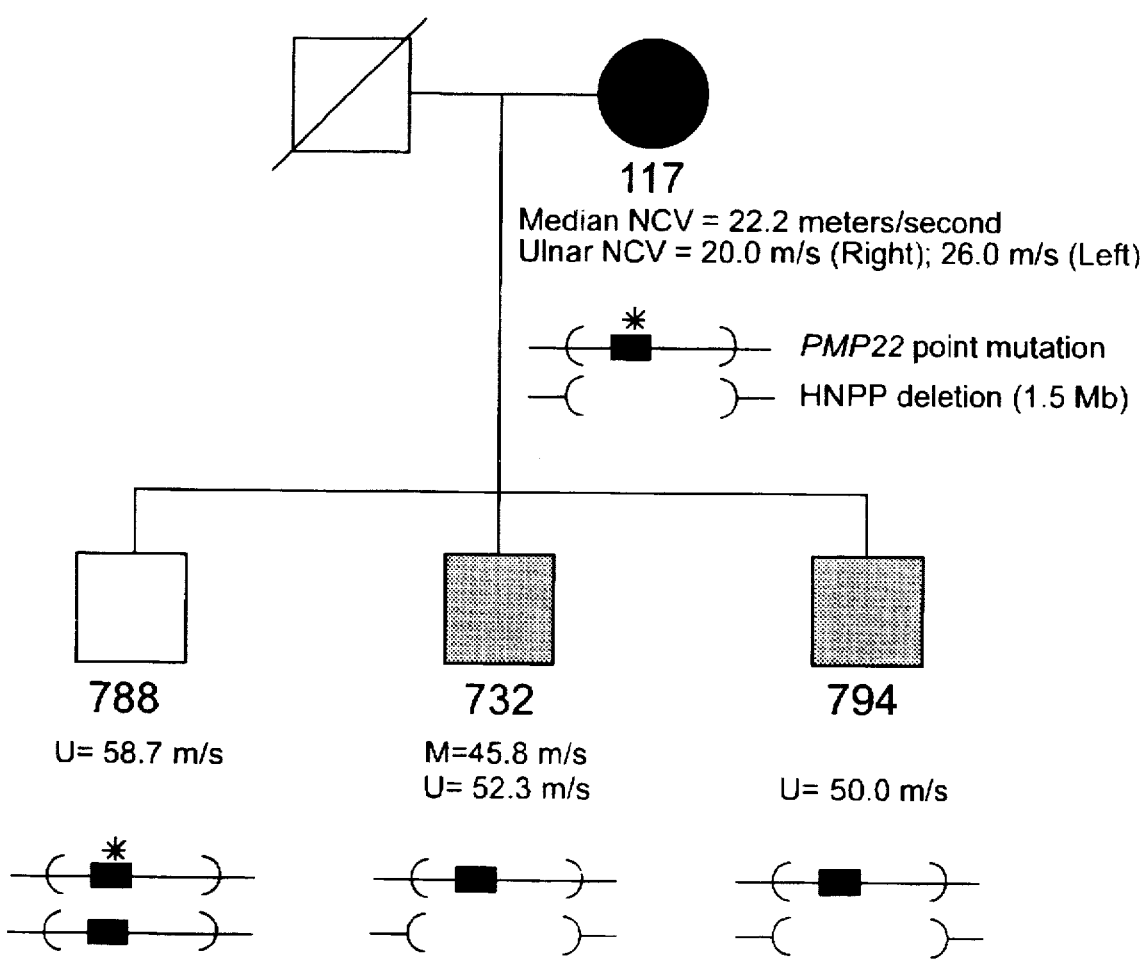

FIG. 12 shows the Pedigree of HOU44 nuclear family. The proband 117 exhibits the clinical phenotype of CMT1 (filled symbol), patients 732 and 794 have the milder clinical phenotype of HNPP (shaded symbols), and individual 788 presents no clinical symptoms of peripheral neuropathy.

Motor nerve conduction velocities (NCV) for each member are shown. The median (M) and ulnar (U) NCV values are symmetrically reduced for CMT1 patient 117, and normal for individual 788. The diagrams below the respective NCV values illustrate the PMP22 genotype for each individual.

Figure 13A:
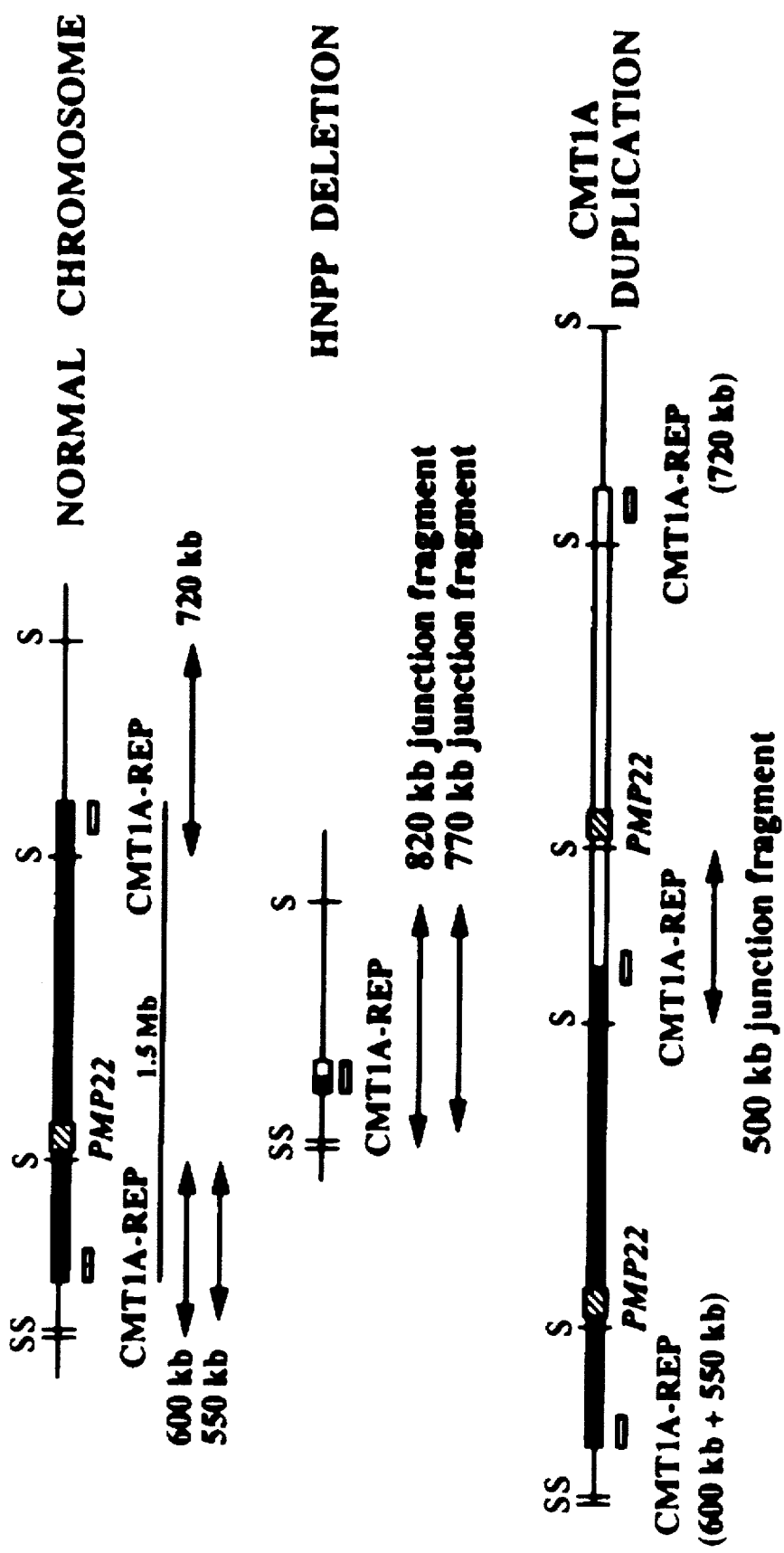
Figure 13B:
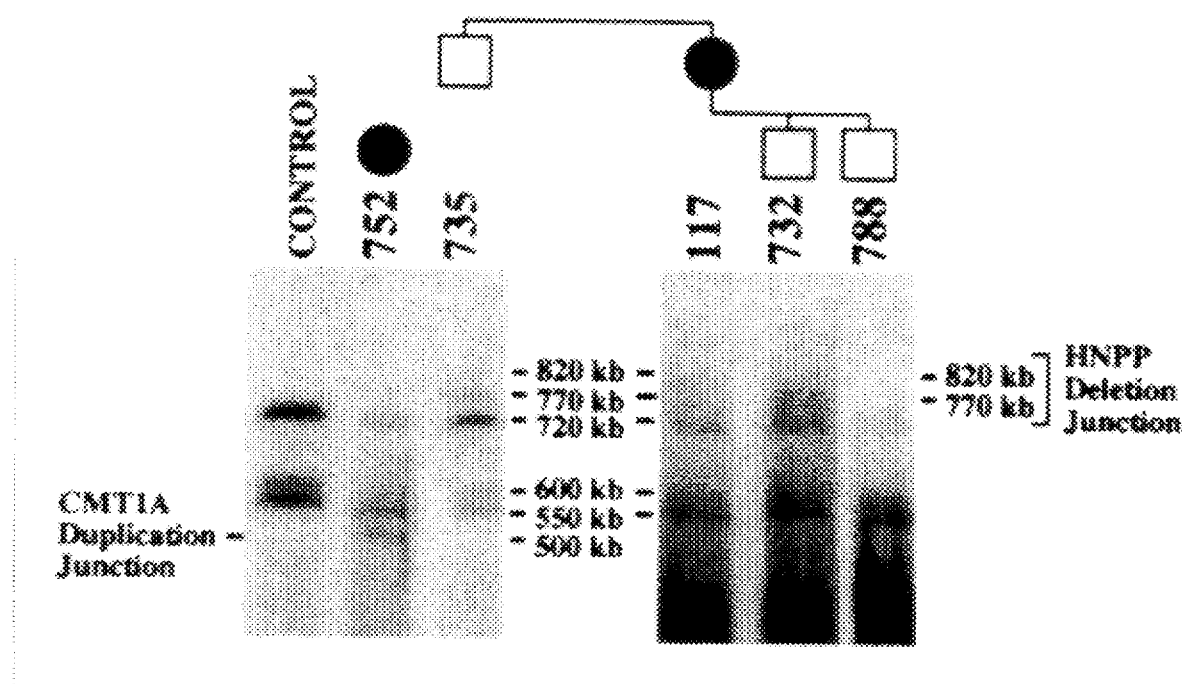

CMT1 patient 117 is hemizygous for PMP22 and carries a point mutation (asterisk) in the PMP22 gene (filled box). The open parentheses on the other chromosome 17 homologue denotes the HNPP deletion which encompasses the PMP22 gene and flanking sequences, totalling 1.5 -Mb of DNA. Individual 788 has one copy of PMP22 with point mutation, and a wild-type copy of PMP22. Patients 732 and 794 each carry the HNPP deletion on one copy of chromosome 17, and a normal copy of PMP22 on the other chromosome 17 homologue. FIGS. 13A and B show the PFGE analysis to detect the HNPP deletionjunction fragments. DNA from HOU44 family members was digested with SacII and fractionated by PFGE followed by Southern hybridization with a probe that maps within the CMT1A-REP repeat flanking the 1.5 -Mb CMT1A duplication/HNPP deletion region. FIG. 13A shows long-range SacII restriction maps of the CMT1A region determined for the normal chromosome 17 and the CMT1A duplication are shown, together with the predicted restriction map in the case of the HNPP deletion. The SacII sites are indicated by S, the stippled box represents the PMP22 gene, and the thin rectangles below the indicated 1.5 -Mb region denote the flanking CMT1A-REP repeats. The sizes of the bands recognized by the CMT1A-REP probe are indicated in each case, with dual junction fragments of 770 kb and 820 kb anticipated for the HNPP deletion. Fig. 13B shows PFGE analysis and hybridization with CMT1A-REP probe demonstrate the predicted HNPP deletion junction fragments in compound heterozygote CMT1 patient 117, HNPP patient 732, and in HNPP patient 735 who is a brother of patient 117. The deletion junction fragments are not seen in HOU44 family member 788 nor in a control individual. Analysis of CMT1A patient 752 containing a de novo duplication demonstrates the corresponding CMT1A duplication junction fragment of 500 kb for comparison.

The drawings and figures are not necessarily to scale and certain features mentioned may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and the spirit of the invention.

Each specific sample to be tested herein for the duplication or deletion in its DNA sequence is derived from genomic DNA. The source of the genomic DNA to be tested can be any medical sample. Some examples of medical samples include blood, semen, vaginal swabs, tissue, mouth wash sample, hair and mixture of body fluids.

As used herein "fragment thereof" refers to an oligonucleotide or DNA probe having sequence identity with a part of a larger oligonucleotide, cosmid or DNA probe, which fragment still hybridizes to the CMT1A-REP sequence. One skilled in the art readily recognizes that fragments of the larger oligonucleotide, cosmid or DNA probe can be made and subcloned by routine methods. Once subcloned, simple screening assays are available to determine if the fragments hybridize to CMT1A-REP.

The duplication in CMT1A disease is characterized by the presence of three copies of the CMT1A-REP sequence on one chromosome of the pair and two copies of the CMT1A-REP on the other chromosome of the pair. The deletion in HNPP disease is characterized by the presence of one copy of the CMT1A-REP sequence on one chromosome of the pair and two copies of the CMT1A-REP sequence on the other chromosome of the pair. Normal individuals will have two copies of the CMT1A-REP sequence on each chromosome of the pair.

As used herein, CMT1A-REP refers to low copy repeat sequences within the CMT1A region and close to the endpoints of and flanking the CMT1A monomer unit. The CMT1A-REP sequences are homologous sequences involved in the genetics of the HNPP/CMT1A disease. The location of the CMT1A-REP sequence is shown in the figures.

One embodiment of the present invention is a method of detecting CMT1A disease in a sample containing DNA from an individual to be tested, comprising the step of measuring in said sample the presence or absence of a DNA duplication using a probe that hybridizes to a CMT1A-REP sequence.

An alternative embodiment of the present invention is a method of detecting HNPP disease in a sample containing DNA from an individual to be tested, comprising the step of measuring in said sample the presence or absence of a DNA deletion using a probe that hybridizes to a CMT1A-REP sequence.

Embodiments of the invention are available to measure the duplication of CMT1A disease or the deletion of HNPP disease. These include dosage measurements of the CMT1A-REP sequence by standard Southern blotting analysis. In a preferred embodiment, a DNA probe which hybridizes to the CMT1A-REP sequence measures the dosage of CMT1A-REP sequences. One skilled in the art readily recognizes that once a sequence has been isolated or identified, probes of various lengths (fragments) can be made to hybridize to the sequence. The fragment must be of sufficient size to distinguish the sequence. Given the examples, one skilled in the art can readily determine the DNA probes which will work in the present invention.

An alternative embodiment to measure the duplication of CMT1A disease or the deletion of HNPP disease is by detecting specific junction fragments using pulsed field gel electrophoresis. This procedure is described by Schwartz, et al., Cold Spring Harbor Symp., Quant. Biol. 47:189–195 (1982). The procedure basically comprises running a standard electrophoresis gel under pulsing conditions. One skilled in the art recognizes that the strength of the field as well as the direction of the field is pulsed and rotated in order to separate megabase DNA molecules. Current commercial systems are computer controlled and select the strength, direction and time of pulse depending on the molecular weight of DNA to be separated.

Another novel aspect of the present invention is the identification and isolation of the CMT1A-REP sequence and the DNA probes used to detect the sequence.

A further aspect of the present invention is a kit to detect CMT1A disease or HNPP disease. The kit includes a DNA probe or probes which hybridize to the CMT1A-REP sequence and container for holding the probe or probes.

The following examples are offered by way of illustration and are not included to limit the invention in any manner. The examples show procedures for isolating and identifying the CMT1A-REP sequence, the probes used and methods of diagnosing CMT1A disease and HNPP disease.

EXAMPLE 1

A YAC Contig Spanning the CMT1A Duplication

YACs corresponding to the CMT1A region were identified from either the St. Louis or CEPH YAC libraries to provide a source of probes for construction of a detailed physical map and for the isolation of genes mapping within the duplication. Probes developed from these YACs as well as previously characterized markers used for physical mapping are given in Table 1.

TABLE 1

DNA Markers in 17p11.2

| Markers | Locus | Description |
| --- | --- | --- |
| FPL25 | | Right end of yc49H7 |
| 1517 | D17S259 | |
| FPL5 | | Right end of ysC24G1 |
| FPL6 | | Left end of ysC8B1 |
| FPL7 | | Right end of ysC8B1 |
| FVG11 | | Right end of ysA217H6 |
| VAW409R3 | D17S122 | |
| PMP-22 | | cDNA |
| FPL24 | | Left end of yc49H7 |
| FPL14 | | Right end of yc181G9 |
| FPL28 | | Right end of yc26A9 |
| FPL19 | | Right end of yc225A3 |
| VAW412 | D17S125 | |
| EW401 | D17S61 | |
| FPL103 | | Alu PCR product from yc225A3 |
| FPL18 | | Left end of yc225A3 |
| FPL10 | | Left end of ysB88B9 |
| VAW411 | D17S124 | |
| EW405 | D17S121 | |
| FPL11 | | Right end of ysB88B9 |
| VAW410 | D17S123 | |

Probes used to define the physical map in this study are listed in Table 1 in order from centromeric (top) to telomeric (bottom) location. "Left" and "Right" ends of YACs denote insert sequences adjacent to the centric and acentric pYAC4 vector arms, respectively, and do not reflect the orientation of the YAC within the map.

Figure 1:
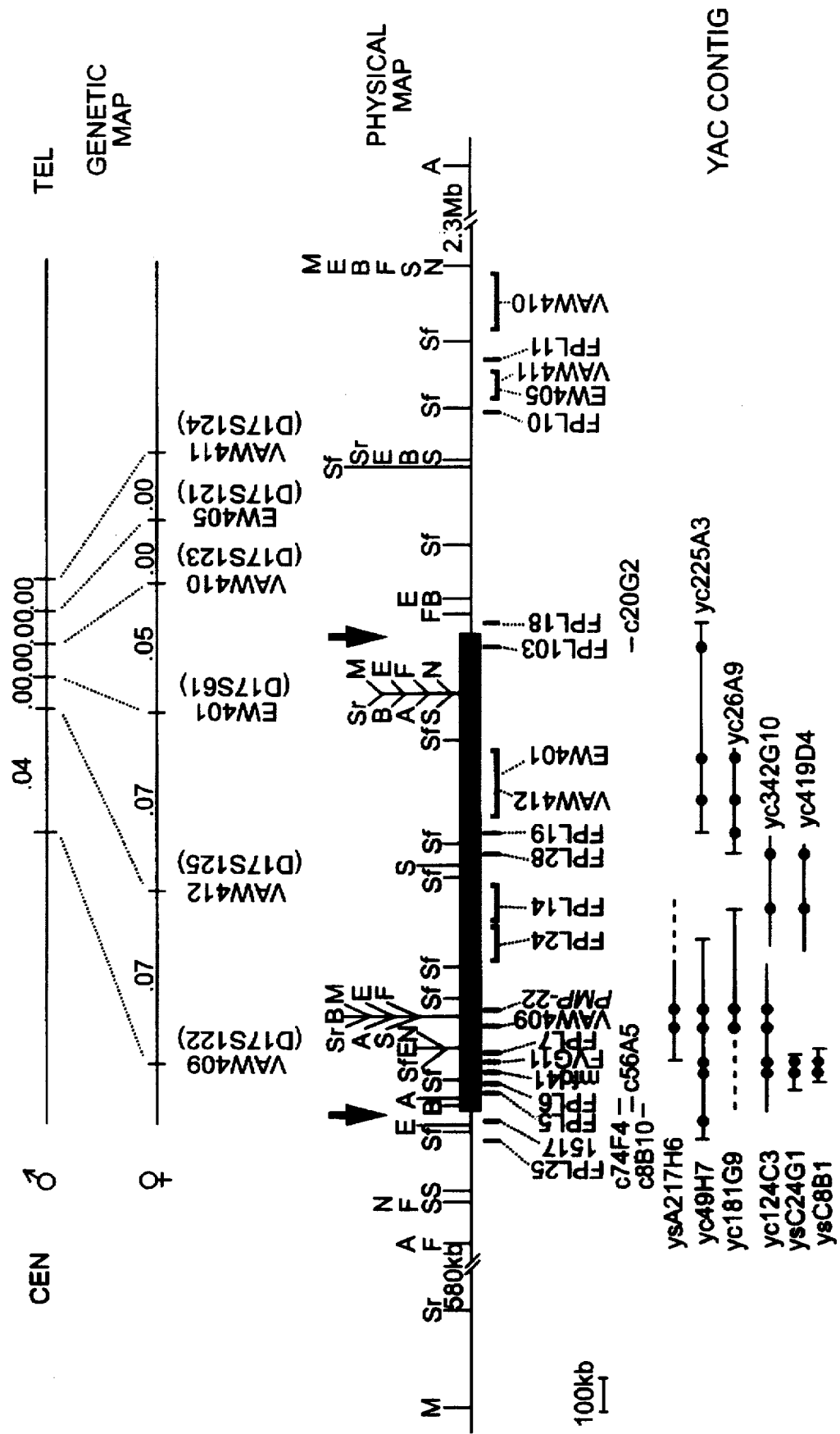
FIG. 1 shows the genetic map, physical map, and YAC contig spanning the CMT1A region. At the top is the published genetic map of the 17p11.2-p12 region. In the center is the physical map deduced from results compiled in Table 1. Boxes show the locations of probes described in Table 1, filled bar indicates the CMT1A duplication region and arrows show the endpoints of the duplication monomer unit. The YAC contig is shown at the bottom. Ends of YACs which were confirmed to be from the CMT1A region of chromosome 17 by mapping to a hybrid mapping panel are shown as vertical lines. Chimeric YACs determined by the same method are shown as dashed lines. Filled circles represent positive hybridization of the YACs to the probe directly above in the physical map. A: AscI; B: BssHII; E: EagI; F: FspI; M: MluI; N: NotI; S: SacII; Sf: SfiI; Sr: SrfI. The YACs labeled "ys" were identified from the St. Louis YAC library while those labeled "yc" were obtained from the CEPH YAC library.

A contig of YACs was constructed by using purified YAC DNA for PCR amplification of known STSs in the region (FIG. 1). These results were then confirmed by hybridization to the markers corresponding to the STSs. ysA217H6, yc49H7, yc181G9, and yc124C3 were originally identified by PCR-STS amplification using primers from VAW409 and ysC24G1 and ysC8B1 were identified by FVG11 primers. yc49H7 contained the STS region from 1517 (D17S259), which is not duplicated in CMT1A patients as well as the STS regions from FVG11, VAW409, and PMP-22 which are duplicated in CMT1A patients (see FIG. 1). These data indicated that yc49H7 spans the proximal endpoint of the CMT1A duplication. The mfd41 STS was contained in yc49H7, yc124C3, ysC24G1, and ysC8B1, placing these YACs as the next most proximal in the contig. These results were confirmed by Southern hybridizations. yc225A3 and yc26A9 DNA were each amplified by STS primers from VAW412 (D17S125) and EW401 (D17S61) and thus were mapped to the distal end of the CMT1A region. The relative orientation of these two markers could not be determined and were mapped in FIG. 1 according to genetic linkage data. The proximal and distal ends of the contig were linked by yc419D4 and yc342G10, which were identified by primers from FPL14, an STS from the end of yc18 1G9. FPL28, the proximal end of yc26A9, hybridized to yc419D4 and yc342G10 confirming the central overlaps as depicted. These results as well as the sizes of the YACs allowed construction of the contig depicted in FIG. 1 and confirmed the size of the CMT1A duplicated region deduced from restriction mapping.

EXAMPLE 2

Physical mapping of the CMT1A duplication region

Figure 2A:
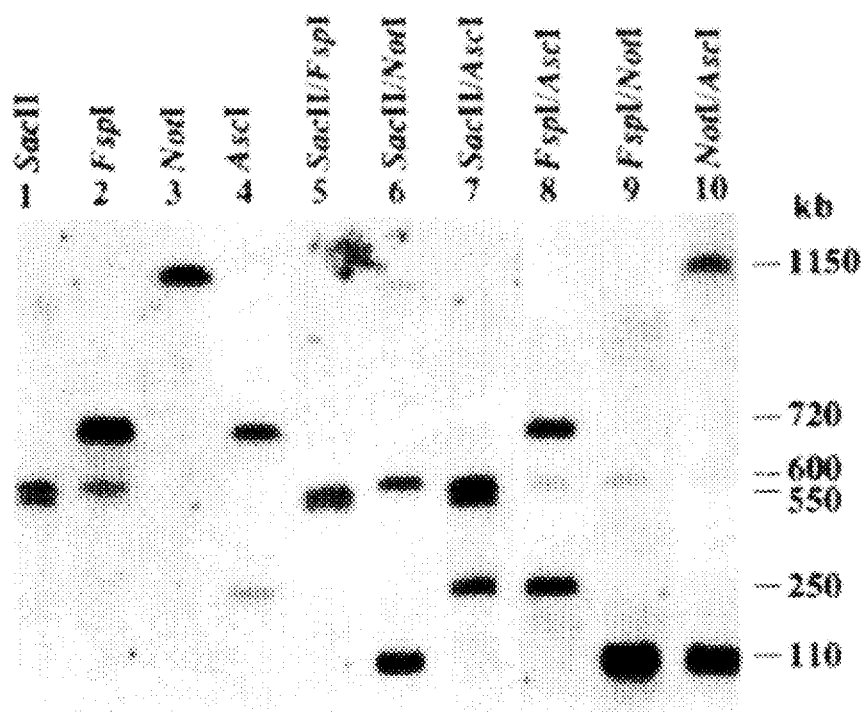
FIGS. 2A–D show a PFGE and Southern blot analysis of the CMT1A region. Agarose plugs prepared from lymphocytes of control individuals were digested with the enzymes SacII, FspI, AscI, NotI, and MluI. Fragments in the 50 kb to 1.2 Mb range were resolved and probed with VAW409 (FIG. 2A) and VAW412 (FIG. 2B). Fragments in the 500 kb to 4 Mb range were separated using recommended parameters on a CHEF mapper and probed with FPL103 (FIG. 2C) and VAW411 (FIG. 2D). The AscI fragments detected by FPL103 and VAW411 are approximately 3.6 Mb.
Figure 2B:
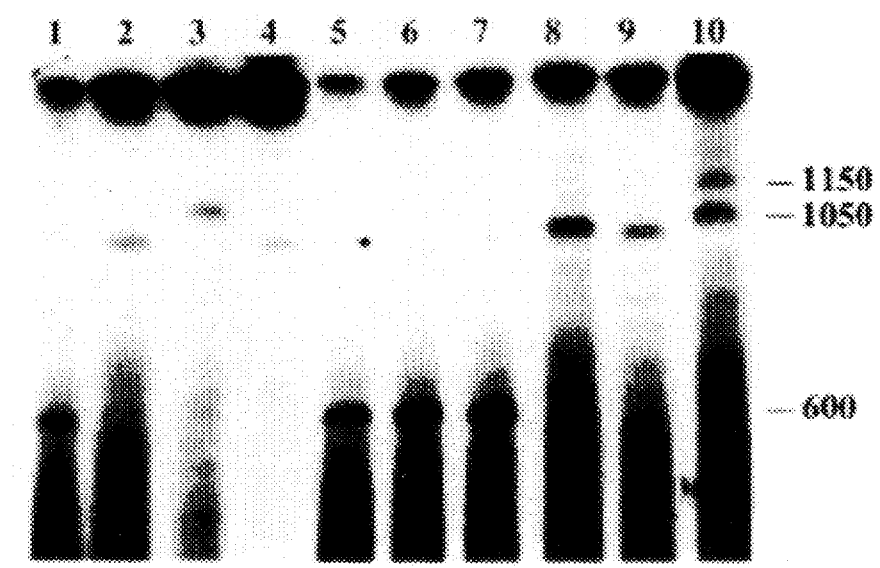

The probes VAW409 (D17S122), VAW412 (D17S125), and EW401 (D17S61) all detect a single 1.15 Mb NotI fragment. Various enzymes were used for single and double digestions of genomic DNA to map these three loci, an example of which is shown in FIG. 2A. VAW409 hybridized to two SacII fragments, 600 kb and 550 kb respectively, which were presumably variant due to methylation differences (FIG. 2A). VAW412 also detected a 600 kb SacII fragment (FIG. 2B). Coincidental comigration of the 600 kb bands detected by these two probes was deduced for the following reasons. First, the relative intensity of the 600 kb band hybridizing to VAW409 was consistently different from that hybridizing to VAW412. Second, in SacII/NotI double digests, VAW409 detected a 110 kb fragment whereas the 600 kb SacII fragment of VAW412 remained unchanged. Third, different patterns resulted after genomic DNA digested with other enzymes was hybridized to VAW409 or VAW412 (FIG. 2 and Table 2).

TABLE 2

Junction Fragments Detected in CMT1A Patients

| | FVG11 | | FPL103 | |
| --- | --- | --- | --- | --- |
| | Control | Patient | Control | Patient |
| SacII | 600 | 600 | 720 | 720 |
| | 550 | 550 | | 500* |
| | | 500* | | |
| FspI | 720 | 720 | 1320 | 1320 |
| | 600 | 600 | 259 | 250 |
| | | 500* | | 500* |
| AscI | 720 | 720 | 3600 | 3600 |
| | 250 | 250 | | 500* |
| | | 500* | | |
| NotI | 500 | 500 | 1320 | 1320 |
| | | 400* | | 400* |
| SacII/NotI | 500 | 500 | 720 | 720 |
| | 450 | 450 | | 400* |
| | | 400* | | |
| SfiI | 125 | 125 | 650 | 650 |
| | | | | 450* |
| BssHII | 320 | 320 | 300 | 300 |
| | | | | 200* |

*junction fragments.

Additional information was obtained from partial digestion with SacII. VAW409 hybridized to two SacII partial fragments, 1050 kb and 1000 kb, corresponding to the 600 kb and 550 kb complete SacII digestion fragments, respectively. A SacII partial fragment of 1050 kb was also detected by VAW412. Considering that these two probes hybridized to two different 600 kb SacII fragments but were contained within the same 1.15 Mb NotI fragment, it was deduced that there was an approximately 500 kb SacII fragment between VAW409 and VAW412. This was confirmed after hybridization with PMP-22, a cDNA encoding the myelin specific protein PMP-22, which is located approximately 50 kb distal to VAW409. The PMP-22 cDNA probe detected the same 1.15 Mb NotI fragment as both VAW409 and VAW412 but hybridized to a 480 kb SacII fragment.

VAW412 hybridized to a 1.05 Mb fragment when the DNA was digested with FspI, AscI, MluI, SrfI, BssHII, or EagI (FIG. 2B and Table 2). There was no alteration in size after double digestion with these enzymes, suggesting that there was a CpG island on each side of VAW412 (D17S125). EW401 (D17S61), the third probe contained within the 1.15 Mb NotI fragment, showed exactly the same restriction hybridization patterns as VAW412, and the smallest fragment shared by these two markers was a 320 kb SfiI fragment. The latter maximum distance between the two probes was confirmed by their coexistence on the 300 kb yc26A9. These results, as well as the sizes of other restriction fragments and the probes used to detect them are summarized in Table 2.

Figure 2C:
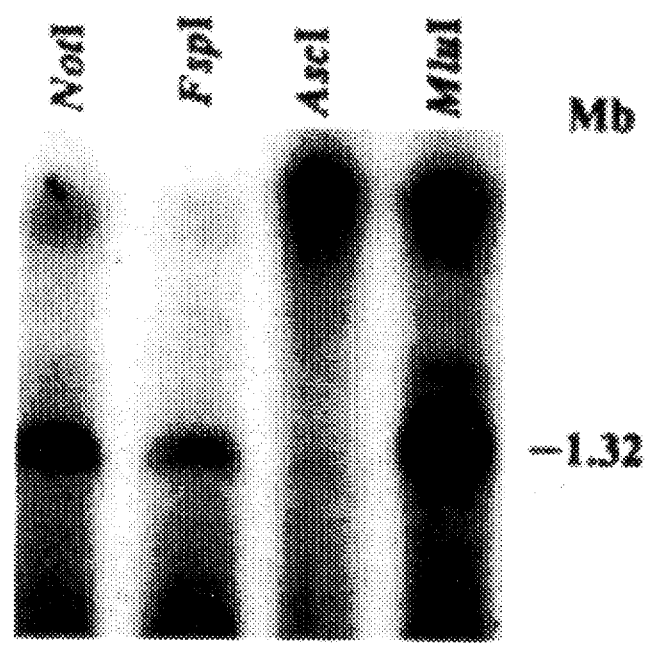
Figure 2D:
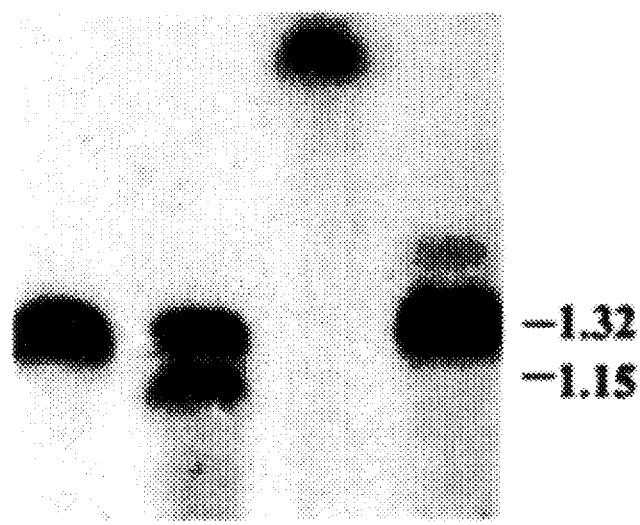

A long range restriction map of the CMT1A region was generated by resolving fragments in the 3.0 Mb range (FIG. 2C and 2D). Previous genetic linkage studies showed that VAW411 (D17S121) which is not duplicated in CMT1A patients, was the next distal marker to VAW412/EW401. VAW411 was physically linked to FPL103, an Alu PCR product derived from the yc225A3 (FIG. 1). FPL103 detected a 1.32 Mb NotI fragment, a 1.32 Mb MluI fragment, a 250 kb FspI fragment and a 1.32 Mb FspI partial fragment (FIG. 2C and Table 2). VAW411 hybridized to the same 1.32 Mb fragments and a 1.15 Mb FspI completely digested fragment (FIG. 2D). Thus, FPL103 and VAW411 were mapped within 1.32 Mb of each other. Markers EW405 (D17S121) and VAW410 (D17S123) were mapped near VAW411, since all three hybridized to the same 620 kb SacII fragment, and EW405 and VAW411 were contained on a single 200 kb fragment after SfiI digestion and double digestion with SacII. Moreover, EW405 and VAW411 were both contained within the 200 kb YAC ysB88B9. At the proximal end, VAW409 detected a 1.3 Mb SrfI fragment and a 1.5 Mb MluI fragment. However, these fragments did not hybridize to probe S6.1-HB2 (D17S445), one of the next known proximal markers which is deleted in patients with the del(17)(p11.) Smith-Magenis syndrome, suggesting that this marker is greater than 1.5 Mb proximal to VAW409. A detailed physical map of the CMT1A region is shown in FIG. 1.

Analysis of the complete rare cutter restriction map of the CMT1A region revealed at least three clusters of sites recognized by enzymes requiring a central CpG dinucleotide (FIG. 1). The two proximal putative CpG islands were found near the end of the CMT1A monomer, one very near the 5'end of the PMP-22 gene, while the third mapped between markers EW401 (D17S61) and FPL103. The presence of two other putative CpG islands suggested that there are at least two other genes within the CMT1A monomer unit in addition to PMP-22.

EXAMPLE 3

A 1.5 Mb tandem duplication is associated with CMT1A

Figure 3A:
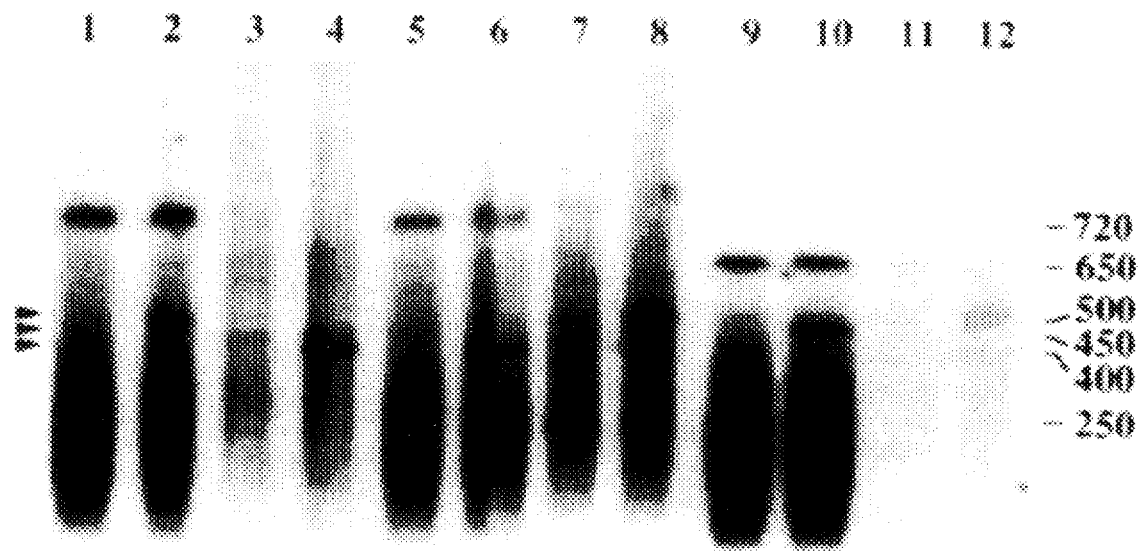
FIGS. 3A and B demonstrate the identification of the CMT1A duplication fragments. Agarose plugs prepared from lymphocytes of a control individual (lanes 1,3,5,7,9) and a CMT1A duplication patient (lanes 2,4,6,8,10) were digested with SacII, NotI, SacII/NotI, FspI, SfiI, AscI and separated by PFGE.
Figure 3B:
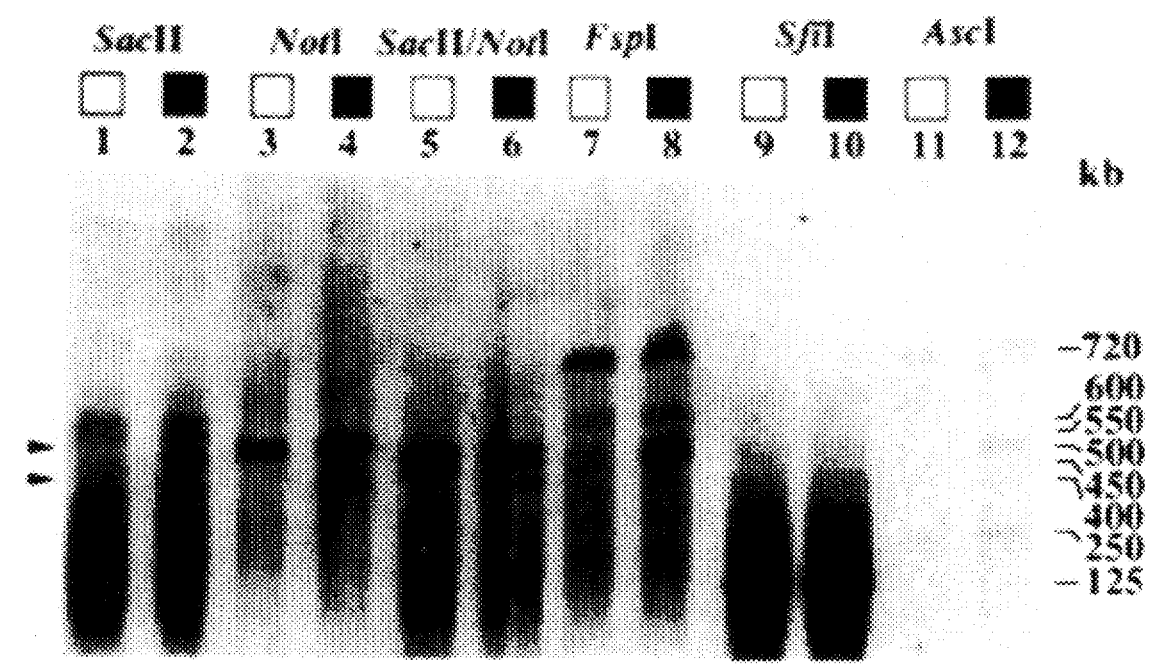

FVG11, a probe which mapped near the proximal end of the CMT1A duplication, detected 500 kb junction fragments in CMT1A patient DNA after digestion with SacII, AscI, and FspI (FIG. 3A). The fact that the junction fragment detected by this probe remained unchanged after digestion with several enzymes led to the hypothesis that the junction was flanked by the recognition sites of these three enzymes. These sites could be the two CpG islands which flank markers VAW412 (D17S125) and EW401 (D17S61) (FIG. 1). Neither VAW412 nor EW401 detected the junction fragment in CMT1A patients, consistent with the presence of a duplication in which both copies of VAW412 and EW401 were flanked by CpG islands. FPL103 was hybridized to CMT1A patient DNA digested with various rare-cutter enzymes since this probe was mapped beyond the CpG island. FPL103 hybridized to the same 500 kb SacII, FspI and AscI junction fragments as FVG11 (FIG. 3B). The possibility that FVG11 and FPL103 were physically contiguous in the CMT1A monomer unit was excluded by both PFGE restriction mapping and the YAC contig. That these two distant probes detected the same junction fragments indicated they were contained in a tandem duplication. A list of junction fragments detected by FVG11 and FPL103 is shown in Table 2.

The endpoints of the CMT1A duplication were mapped by determining which probes were duplicated, or which probes identified the 500 kb SacII junction fragment, by analyzing genomic DNA from CMT1A patients with the duplication and comparing this to unaffected control individuals. At the proximal end, FPL5 detected the 500 kb SacII junction fragment whereas; 1517 (D17S259), the next proximal marker in the region did not. The proximal endpoint of the CMT1A duplication thus mapped between these two markers. At the distal end of the CMT1A duplicated region FPL103 detected the junction fragments given in Table 2 whereas FPL18, the next most distal marker, did not detect a junction fragment. Therefore, FPL18 was mapped outside the duplicated region. The distance between 1517 and FPL18 was estimated to be 1.5 Mb as measured by the size of the YAC contig and by physical mapping. The size of the CMT1A monomer unit could also be deduced by adding the size of the junction fragment (NotI=400 kb; FspI=500 kb, Table 2) and the size of the restriction fragment flanked by CpG islands and detected by VAW412 and EW401 (NotI= 1.15 Mb; FspI=1.05 Mb, Table 2). Thus the maximum size of the region duplicated in CMT1A is approximately 1.5 Mb.

EXAMPLE 4

Very Low Copy Repeats Present in 17p

Figure 4A:
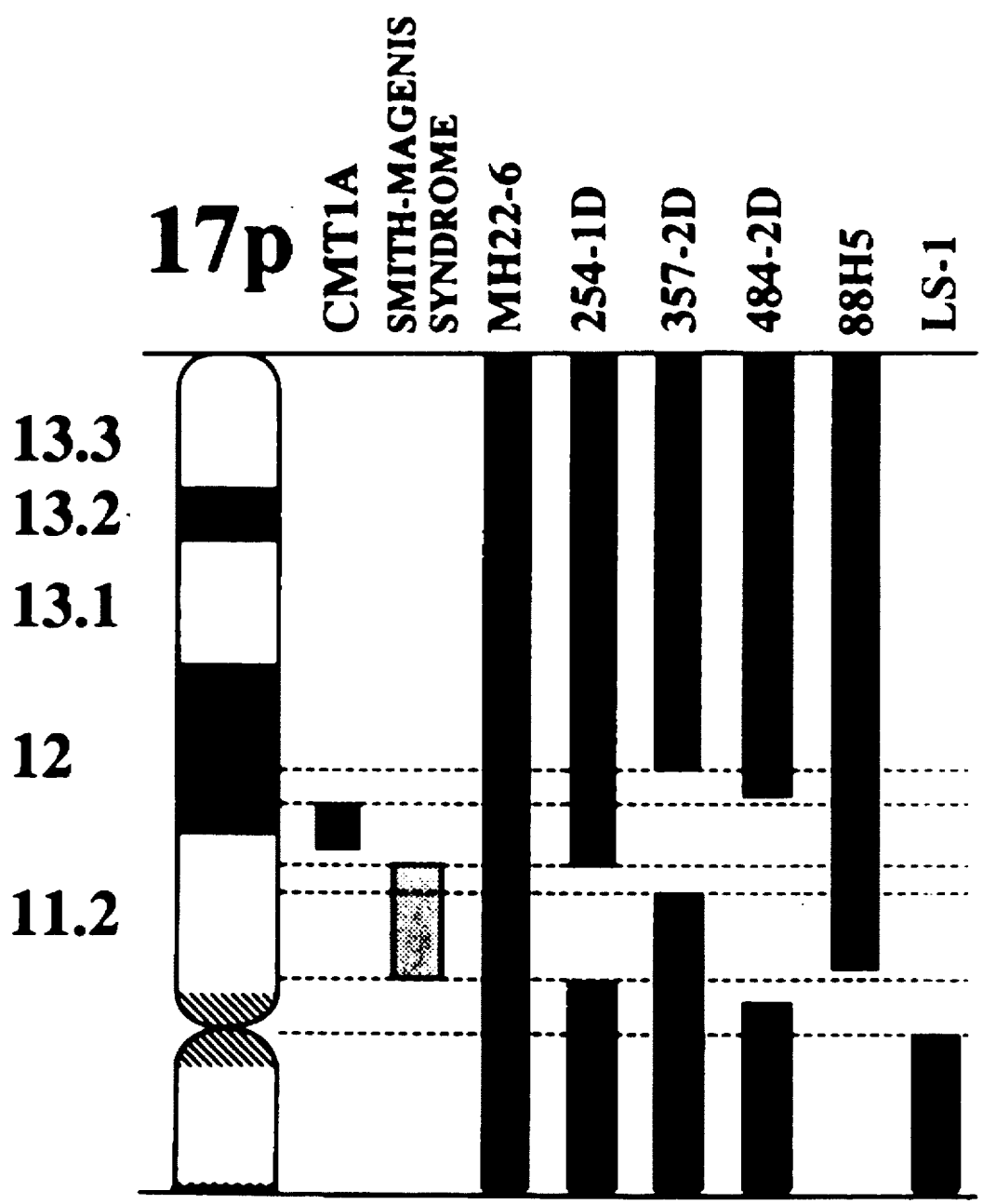
FIGS. 4A–D show localization of DNA probes to the 17p11.2-p12 region.
Figure 4B:
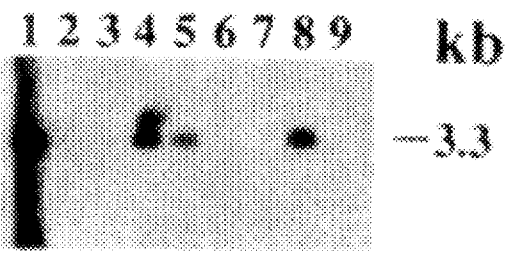
Figure 4C:
Figure 4D:
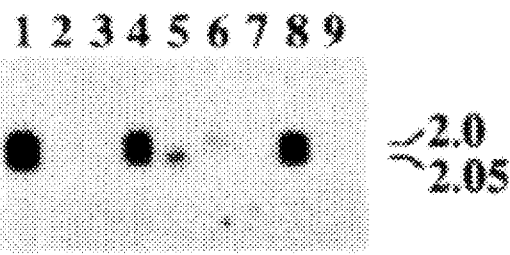

Probes generated in these studies were assigned to the 17p11.2-p12 region by hybridization to a somatic cell hybrid panel. This panel contained hybrids retaining either deleted derivatives of human chromosome 17 or chromosome 17 with a translocation breakpoint, thereby allowing probes to be mapped relative to the CMT1A region. As shown in FIG. 4B, FPL14 hybridized to somatic cell hybrids retaining the CMT1A region (hybrids MH22-6, 254-1D, and 88H5), but not to hybrids deleted for the CMT1A region (357-2D, 484-2D, and LS-1). VAW411 (FIG. 4C) was also absent in the hybrids deleted for the CMT1A region except for hybrid 484-2D, mapping this marker just distal to the CMT1A duplication. However, probe FPL5 (FIG. 4D) detected the same two fragments in total human DNA as in hybrids MH22-6 and 88H5. The fact that two bands were seen in the monochromosomal hybrid MH22-6 indicated that FPL5 mapped to two loci on 17p instead of detecting a simple polymorphism. This was confirmed by somatic cell hybrids 254-1D and 357-2D which retained each locus individually. Both loci were deleted in hybrid 484-2D (FIG. 4D). Therefore, FPL5 was assigned to two loci in 17p11.2-p12, one proximal to the CMT1A region (present in hybrid 357-2D), and one within the CMT1A region (present in hybrid 254-1D). Physical mapping and YAC contig data further demonstrated that one of the loci was within the CMT1A monomer unit (FIG. 1). By PFGE, FPL5 detected the same 600 kb and 550 kb SacII fragments as VAW409 as well as an additional 250 kb fragment not detected by VAW409 (Table 2). Similar results were obtained with probes 1517 (D17S259) and FPL25, the proximal end of yc49H7 (data not shown).

EXAMPLE 5

Figure 5:
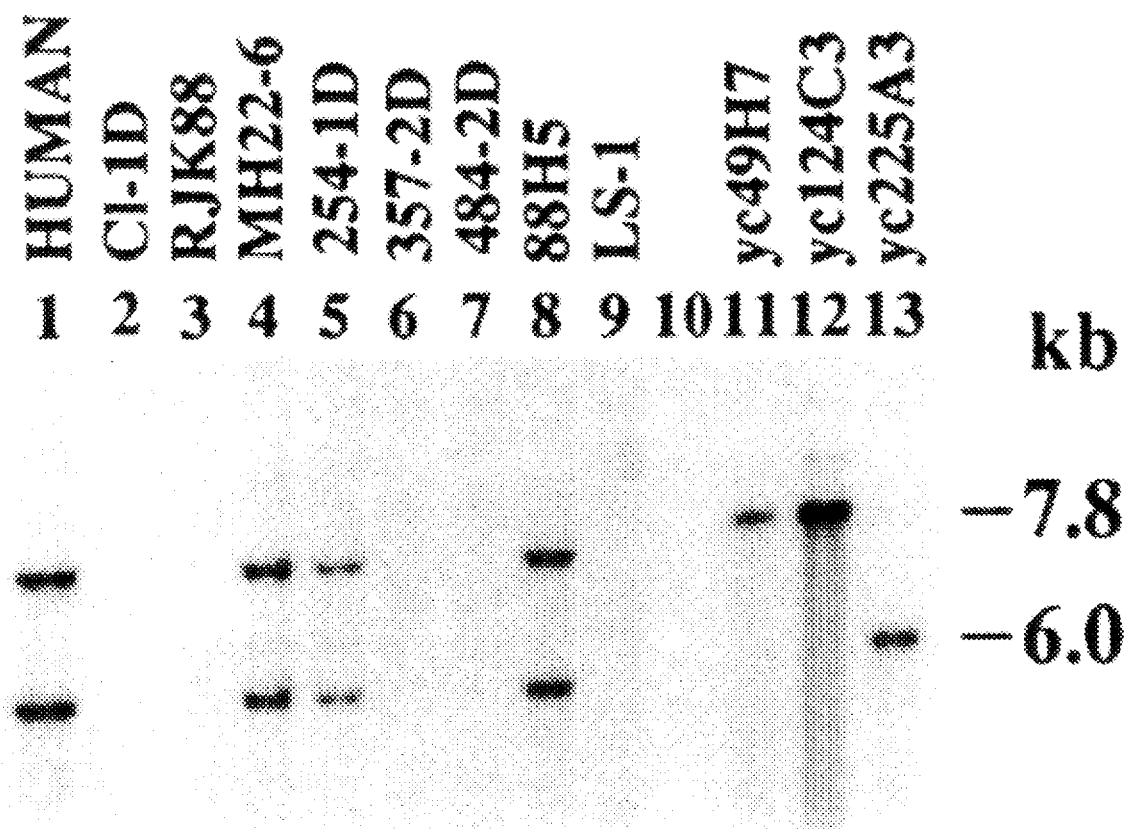
FIG. 5 shows the CMT1A duplication monomer unit is flanked by CMT1A-REP. 5.5 μg total human DNA, (lane 1), 15.5 μg hybrid DNA and 0.1 μg YAC DNA were digested with EcoRI and the Southern blot hybridized to CMT1A-REP. Lanes 2–9 correspond to hybrids C1–1D, RJK88, MH22-6, 254-1D, 357-2D, 484-2D, 88H5, and LS-1. Lane 10 is a blank lane and lanes 11–13 correspond to yc49H7, yc124C3, and yc225A3. Molecular weight markers are shown on the right. The bands in lanes 1–8 containing genomic DNA appear to migrate faster than those in lanes 11–13 containing YAC DNA secondary to the amount of DNA loaded.
Figure 7:
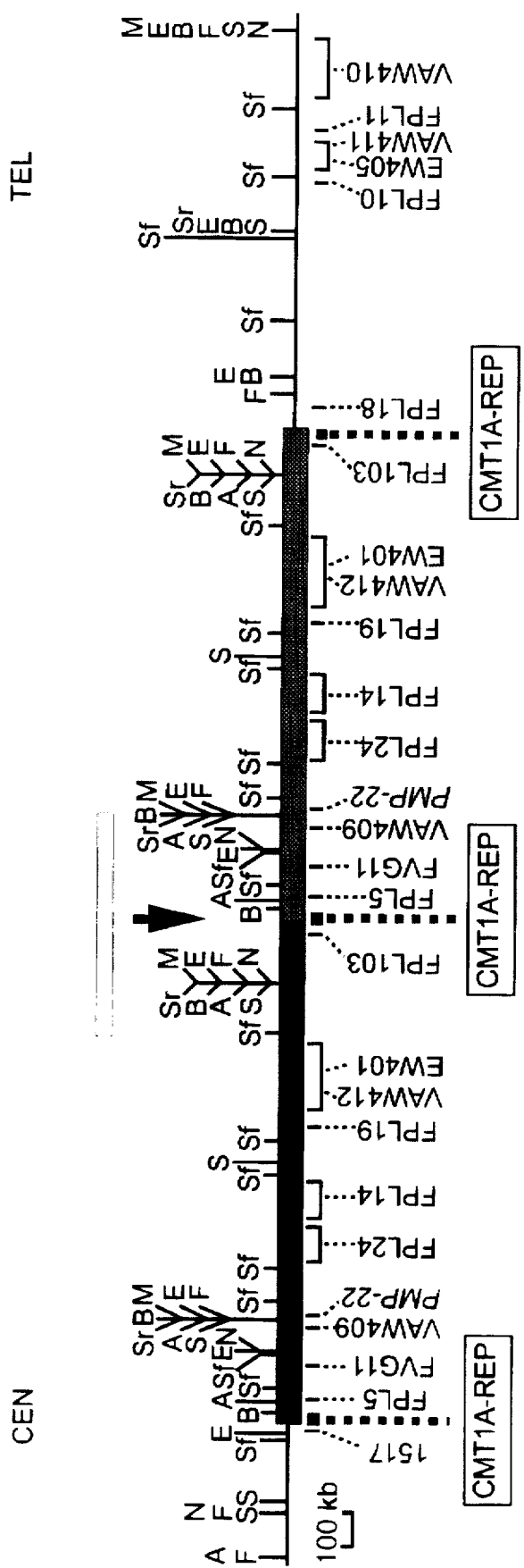
FIG. 7 is a schematic representation of the CMT1A duplication is a tandem duplication of 1.5 Mb in 17p11.2-p12. The duplication of 17p11.2-p12 found in CMT1A patients is depicted. Boxes denote various markers (as in FIG. 2) and the arrow denotes the junction point. The long open box below depicts the region from which the junction fragments listed in Table 2 were obtained.

CMT1A-REP is A DNA Repeat Flanking the CMT1A Duplicated Region and is Present in an Additional Copy in CMT1A Patients To study the sequences comprising the CMT1A duplication junction in more detail, cosmids corresponding to yc225A3, which spans the distal junction point, were isolated from a human chromosome 17 cosmid library as described. One of these cosmids, c20G2 (FIG. 1), contained sequences which hybridized to two regions within the CMT1A monomer unit. A 1.8 kb EcoRI fragment from this cosmid end was hybridized to the chromosome 17 somatic cell hybrid mapping panel (FIG. 5). This probe identified both a 7.8 kb and a 6.0 kb EcoRI restriction fragment in total human DNA, the chromosome 17 monochromosomal hybrid MH22-6, and hybrids 254-1D and 88H5, but was negative in the rodent control lanes, and in hybrids 357-2D, 484-2D, and LS-1 (FIG. 5). Thus, both of these loci mapped within the CMT1A region. These two loci were separated and localized more precisely by hybridization to the YACs. These low copy repeat sequences, called CMT1A-REP, were present in a 7.8 kb EcoRI fragment in proximal yc49H7 and yc124C3 and in a 6.0 kb EcoRI fragment in distal yc225A3 and did not hybridize to any additional YACs in the CMT1A contig (FIG. 5). These YACs contain the proximal and distal CMT1A duplication endpoints. Moreover, CMT1A-REP hybridized to PFGE fragments recognized by the distal probe FPL103. In addition, it also detected fragments identified by several proximal probes including FVG11, FPL6 and FPL5, consistent with the results shown in FIG. 7. Thus, CMT1A-REP is close to each endpoint of the CMT1A monomer unit.

Figure 6:
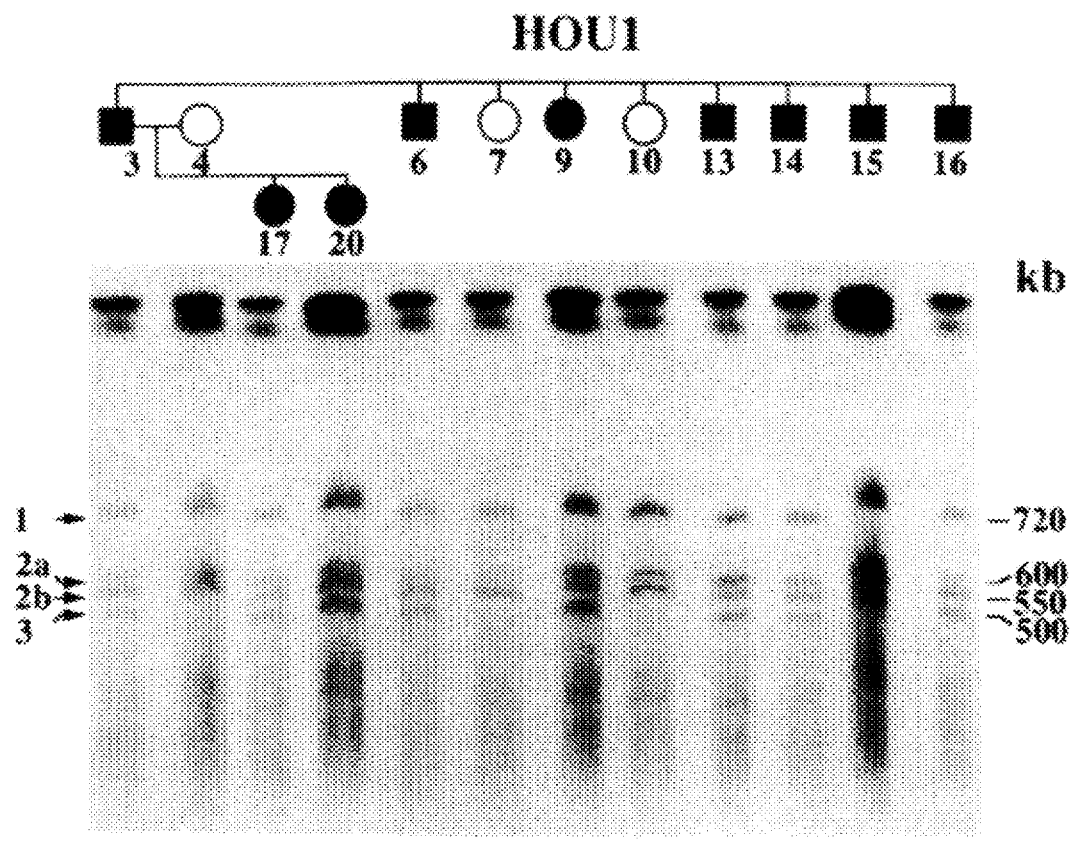
FIG. 6 demonstrates that CMT1A-REP is present in three copies on the CMT1A chromosome. DNA plugs from pedigree HOU1 were digested with SacII and hybridized to CMT1A-REP. The two bands seen at 600 and 550 kb (2a and 2b) are routinely seen in patients and controls and are thought to be due to methylation differences. Molecular weight markers are shown at right.

The fact that the CMT1A monomer unit was flanked by these repeats suggests that the CMT1A duplication arose after unequal crossing over between homologous flanking sequences. According to this model, CMT1A patients should have three copies of the CMT1A-REP on the CMT1A (duplicated) chromosome but the normal chromosome should contain only two copies. This hypothesis was tested by hybridizing the CMT1A-REP probe to CMT1A patient DNA (FIG. 6) and control DNA digested with SacII from pedigree HOU1. In all samples this probe detected the same 720 kb SacII fragment as probe FPL103 (FIG. 6 "1") and also hybridized to the same 600 kb and 550 kb SacII fragments detected by FVG11 (FIG. 6 "2a" and "2b"). This was consistent with the data in FIG. 5 indicating that this repeat is found near each end of the CMT1A monomer unit. In patients with the CMT1A duplication, the CMT1A-REP probe detected the same two loci as in controls plus a third novel fragment, the same 500 kb junction fragment detected by FVG11 (FIG. 6 "3"). Furthermore, the intensity of the hybridization signal of band 3, the junction fragment, was approximately half that of band 1 or band 2 (FIG. 6 "2a" plus "2b"), consistent with the presence of two copies of this repeat on the normal chromosome and of three copies on the CMT1A chromosome in pedigree HOU1. Identical results were obtained using unrelated CMT1 patients with the CMT1A duplication. Similarly, when genomic DNA from CMT1A patients and controls was digested either with NotI or FspI the expected size restriction fragments were observed.

To further demonstrate that the CMT1A-REP flanks the CMT1A duplication monomer unit a cosmid containing part of CMT1A-REP, c74F4 (FIG. 1), was isolated. The cosmid c74F4 was one of several cosmids identified by screening a flow-sorted human chromosome 17 cosmid library with the 1.8 kb EcoRI fragment from c20G2. Both ends of c74F4 were isolated. One end was mapped within the CMT1A duplication. The other end of c74F4 mapped to 17p11.2 outside CMT1A-REP and was not duplicated in patients with the CMT1A duplication. Thus, this cosmid spanned the proximal end of the CMT1A duplication (FIG. 1). Analysis of the junctions between CMT1-REP and proximal flanking unique sequences in cosmids c74F4 and c20G2 is consistent with CMT1A-REP being a tandem repeat and not an inverted repeat. The CMT1A-REP DNA sequence was also used to probe a "zoo blot" to determine evolutionary conservation. The probe hybridized to the expected two fragments in human genomic DNA and to one fragment in monkey genomic DNA. Lack of hybridization to bovine, murine, rabbit, or Drosophila DNA suggested that CMT1A-REP is not an expressed sequence. A diagram of the duplicated CMT1A chromosome is given in FIG. 7 including the three CMT1A-REP sites. The maximum size of the tandem duplication is approximately 3 Mb. The open bar beneath the duplicated chromosome depicts the region from which the junction fragments listed in Table 2 were identified.

EXAMPLE 6

YAC Library Screening

YAC libraries from St. Louis and from CEPH were screened for positive clones in the Baylor Human Genome Center YAC Cloning Core facility by a PCR-based strategy. YACs denoted by "ys" were isolated from the St. Louis library and YACs denoted by "ye" were isolated from the CEPH library. The positive YACs for each marker were confirmed by Southern hybridization with the same probe from which the STS primer set was designed.

EXAMPLE 7

Isolation of YAC Ends and Internal Fragments

YAC ends were isolated by Alu-vector PCR, or alternatively by vectorette PCR. FPL14 was made by Alu-vector PCR using a biotinylated oligonucleotide complementary to the left vector arm of yc181G9 and Alu PDJ34 oligonucleotide. The PCR product was purified over streptavidin beads (Dynal, Inc.) and sequenced directly, using the Alu PDJ34 oligonucleotide as primer. The sequence obtained from FPL14 was used to design the following primers for PCR amplification: IMG 8052: GGCTTCTCGCTCTGATCATA; IMG 8053: GCTGTCTTATGTTCTGCATGG. The product of this amplification is 170 bp. To obtain internal fragments, Alu PCR was performed using 10 ng whole cell yeast DNA containing the YAC of interest. The desired internal or end fragments were isolated from low melting agarose and labeled directly for use as probes. Probes were hybridized to a somatic cell hybrid panel developed from del(17)(p11.2-p11.2) or del(17)(p11.2-p12) patients for mapping relative to the CMT1A region. Chimeric YACs were identified by hybridization of the ends to a human chromosome 17 somatic cell hybrid panel which either included or excluded the probe from the CMT1A region. Not every YAC end was tested (FIG. 1); therefore yc124C3, yc419D4, yc342G10, and yc26A9 could be chimeric.

EXAMPLE 8

Pulsed Field Gel Electrophoresis

High molecular weight DNA was isolated in agarose plugs from Epstein-Barr virus-transformed lymphoblastoid cell lines established from controls and patients, or directly from peripheral blood. For the latter, 7 ml whole blood was layered over 7 ml Ficoll-Paque (Pharmacia) and centrifuged at 1500 rpm for 30 minutes at room temperature. The white blood cell layer was removed into a new tube and washed once with Hank's buffered saline: solution (HBSS) (Bioproducts). Cells were counted and encapsulated in 0.8%, Incert agarose (FMC) containing 10 mM TrisHCl pH 7.8, 20 mM NaCl, 100mM EDTA pH 8.0 at a concentration of $1.25 \times 10^7$ cells/ml. One-fourth of the plug was digested under conditions recommended by the manufacturers. Twenty units BssHII, EagI, SfiI, SacII, FspI, MluI, SrfI and NotI and 3 units AscI were used per reaction. For double digestions all traces of the first enzymes were removed by two to three 2 ml washes of TE (pH7.5) before re-equilibrating the plugs with the buffer for the second enzyme. To ensure that both enzymes in the double digestion were active, each experiment was accompanied by two single digestions using the enzymes separately. All rare cutter enzymes were from New England Biolabs except SrfI, which was purchased from Stratagene.

DNA was separated using a CHEF mapper (Biorad). Fragments from 50 kb to 1200 kb were separated by electrophoresis through 1.0% agarose (ultrapure, BRL) at 200 volts for 24 hours at 14° C. in 0.5×TBE (45mM Tris-Borate, 1mM EDTA), using 50 seconds to 90 seconds ramping pulse time and an included angle of 120° C. The separations of larger DNA fragments were performed using the appropriate programs from the CHEF mapper.

EXAMPLE 9

Southern Blotting and Hybridization

After treatment with 0.25N HCl for 15 minutes, pulsed field gels were blotted onto Zeta-probe GT nylon membrane (Biorad). Probes were successively hybridized to the same filters to ensure accurate data. Filters were stripped for reuse by soaking in 2 mM Tris-HCl pH8.0, 0.2 mM EDTA pH 8.0, 0.1% SDS at 80° C. for 20 minutes.

EXAMPLE 10

Somatic Cell Hybrid Panel

The somatic cell hybrid panel for regional assignment of 17p marker:, is known in the art. Except for 484-2D which was derived from a del(17)(p11.2p12) Smith-Magenis syndrome patient having a larger deletion that extended more proximal than the deletion of hybrid 254-1D and through the CMT1A duplicated region. Probes are localized near the CMT1A region if they are present in human, MH22-6, 88H5, 254-1D but absent in 357-2D and 484-2D.

EXAMPLE 11

Alternative Hybridizations and Dosage Analysis

High molecular weight DNA was isolated from peripheral blood or lymphoblasts by standard methods. Restriction enzyme digests were carried out according to the manufacturer's instructions. Gel electrophoresis, including pulsed-field gel electrophoresis (PFGE) and Southern transfer to nylon membranes (Hybond M. Amersham) are known in the art. Probes were labeled with $^{32}$P to high specific activity ($5 \times 10^8$ to $5 \times 10^9$ cpm) by the random hexamer-primer method.

Hybridizations were carried out overnight at 65° C. in a solution containing 10% PEG, 7% SDS, 1.5X SSPE and 5X Denhardt's reagent and washed to a stringency of 0.1XSSC/0.1% SDS for 5–15 min. Filters were placed against X-ray film (XOMAT-AR, Kodak) overnight at −70° C.

EXAMPLE 12

Dosage analysis of the CMT-REP repeat in CMT1A and HNPP

Figure 8:
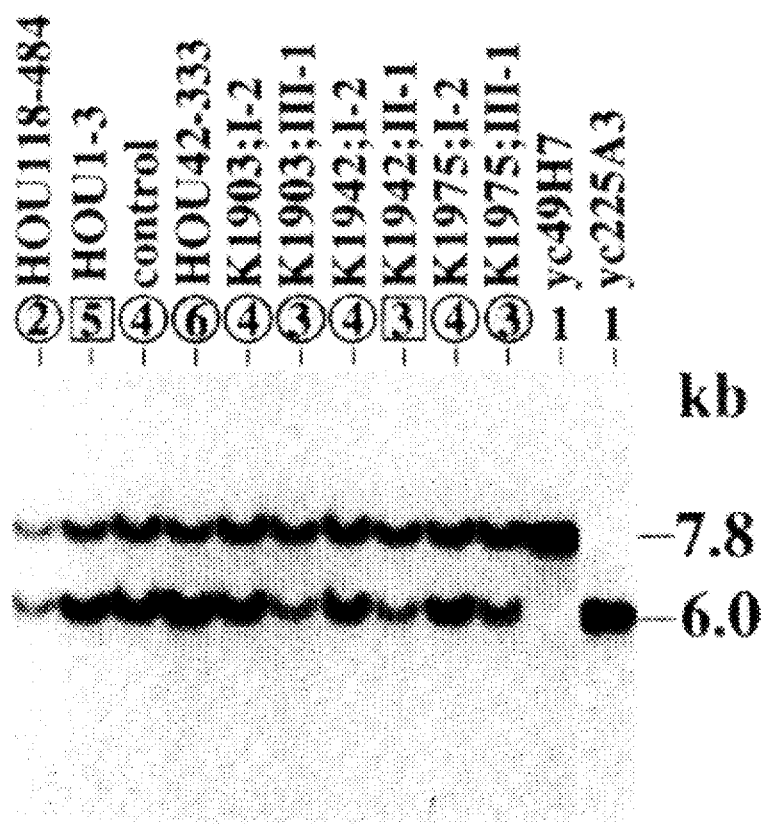
FIG. 8 shows the CMT1A-REP repeat in CMT1A duplication and HNPP deletion patients. All patient and control genomic DNAs, as well as YAC yc49H7 which spans the proximal CMT1A duplication junction and YAC yc225A3 which spans the distal junction, were digested with EcoRI. Equal amounts of DNA were loaded per lane. This Southern blot was hybridized with a 1.8 -kb EcoRI end fragment from cosmid c20G2. This probe identifies a 7.8 -kb EcoRI fragment in the proximal (centromeric) CMT1A-REP repeat and a 6.0 -kb EcoRI fragment in the distal (telomeric) CMT1A-REP repeat. Above each lane standard pedigree symbols are used with circles representing females, squares representing males, and shaded symbols are used referring to affected individual. The arabic numerals inside the symbols refer to the putative number of copies of the CMT1A-REP repeat in each individual. Lanes 5–10 are respectively an unaffected and affected family member from three different HNPP pedigrees: K1903, K1942, and K1975. Note that only affected individuals display decreased dosage of the lower 6.0 -kb EcoRI fragment relative to the upper 7.8 -kb fragment. Lane 1 contains DNA from a Smith-Magenis syndrome [del(17)(p11.2p12)] patient who is deleted for the entire CMT1A/HNPP region including both the proximal and distal CMT1A-REP repeat sequences. Lanes 2 and 4 contain DNA and CMT1A duplication and homozygous CMT1A duplication patients respectively. Lane 3 contains DNA from a normal control individual with no family history of neurological disease.

The results of hybridization of a 1.8-kb EcoRI fragment that detects the CMT1A-REP repeat sequence to EcoRI-digests of DNA from normal, CMT1A and HNPP patients are shown in FIG. 8. As shown in FIG. 8, this CMT1A-REP repeat probe identifies two sequences on chromosome 7:11.2-12. A 7.8-kb EcoRI fragment is localized to the proximal CMT1A duplication monomer region as evidenced by hybridization to a yeast artificial chromosome (YAC) clone which spans the proximal duplication breakpoint region (yc49H7). A 6.0-kb EcoRI fragment maps to the distal CMT1A region and gives a signal when hybridized to a HAC clone which spans the distal CMT1A duplication breakpoint (yc225A3). In unaffected persons (control, K1903;I-2, K1942;I-2 and K1975;III-1) four copies of the CMT1A-REP repeat sequence are present, a proximal and distal CMT1A-REP repeat on each chromosome 17 homologue and the hybridization intensities of the 6.0 and 7.8-kb fragments are approximately equal. Hybridization of the CMT1A-REP probe to EcoRI-digested DNA from a patient with CMT1A(HOU1-3) and to a patient to is homozygous for the CMT1A duplication (HOU42-333) showed increased hybridization intensities of the 6.0-kb fragment relative to the 7.8-kb fragment, indicating the gain of an additional copy of the 6.0-kb fragment on the CMT1A-duplicated chromosome. Hybridization of the CMT1A-REP repeat probe to EcoRI-digested DNA from three unrelated patients with HNPP (K1903;III-1, K1942;II-1, K1975;III-1) detected reduced hybridization intensity of the 6.0-kb fragment relative to the 7.8-kb fragment. This observation indicates that a copy of the 6.0-kb fragment is missing on the deleted chromosome in patients with HNPP. This analysis was performed in a masked fashion with the laboratory carrying out the interpretation of CMT1A-REP repeat copy number in the HNPP pedigrees being unaware of patient clinical status.

EXAMPLE 13

Analysis of the CMT1A-REP repeat in de novo CMT1A and HNPP

Figure 9:
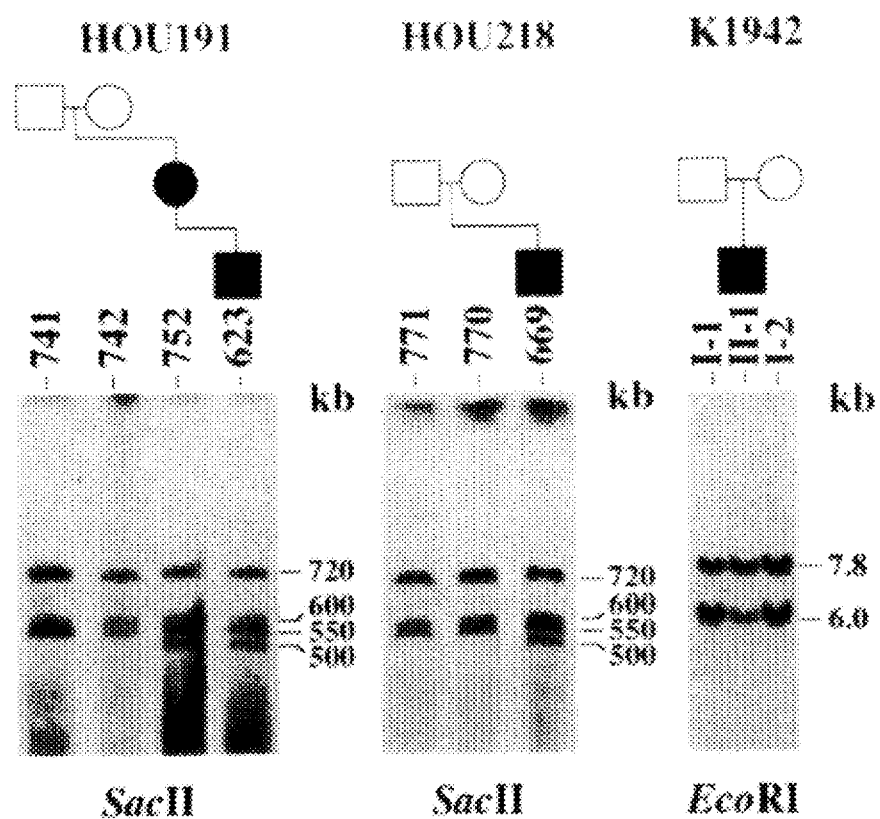
FIG. 9 demonstrates recombination involving CMT1A-REP in de novo CMT1A duplication and de novo HNPP. Pedigrees HOU191 and HOU218 are de novo CMT1A duplication families while pedigree K1942 is a de novo HNPP deletion family. The probe used for hybridization in all three Southern blots recognizes the CMT1A-REP repeat and is the same probe described in FIG. 8. Restriction fragment sizes are given at the right while the enzyme used for digestion is shown below the gel. The two left panels are from pulsed-field gel electrophoresis (PFGE) while the right panel is from a standard agarose gel electrophoresis. Hybridization of the CMT1 A-REP probe to DNA from normal persons detects two fragments in the proximal region (600/550 -kb) and one fragment in the distal region (720 -kb) of the CMT1A duplication monomer unit. Note the appearance of the 500 -kb duplication-specific junction fragment in the de novo CMT1A duplication patients. The same CMT1A-REP probe hybridizes to two different EcoRI fragments in the proximal (7.8 -kb) and distal (6.0 -kb) CMT1A-REP repeat (FIG. 8). Note the decreased dosage of the 6.0 -kb EcoRI fragment in the de novo HNPP deletion patient compared to his parents.

The results of from hybridization of the CMT1A-REP to DNA from patients with de novo CMT1A and HNPP are shown in FIG. 9. In unaffected persons the CMT1A-REP probe detects a 720-kb SACII fragment from the distal CMT1A region and a 600 -kb and 550 -kb fragment from the proximal CMT1A region. These two fragments detected within the proximal CMT1A region result from variable degrees of methylation at a SacII site located at the 5'region of the CMT1A duplication monomer. Similarly to the above discussion of patients with inherited, duplication CMT1A, patients with de novo CMT1A have a novel 55-kb SACII fragment detected with the CMT1A-REP repeat. As shown in FIG. 9 analysis in a patient with de novo CMT1A have a novel 500-kb SacII fragment detected with the CMT1A-REP repeat. As shown in FIG. 9 analysis in a patient with de novo HNPP detected reduced hybridization of the 6.0-kb EcoRI fragment, indicating a loss of this fragment, similar to that observed in inherited HNPP (see FIG. 8). A model for unequal crossing over mediated through the CMT1A-REP sequence resulting in the duplicated and deleted chromosome is presented in FIG. 10. As shown in FIG. 11, the CMT1A-REP sequence detects two predicted novel SacII fragments of 820 and 770-kb in a de novo deletion patient. Similar fragments were detected with the CMT1A-REP sequence in the analysis of 3 unrelated patients with inherited HNPP.

EXAMPLE 14

Mechanism of Duplication/Deletion

Unequal crossing-over during meiosis is a proposed mechanism for generating the DNA duplication in CMT1A and the deletion in HNPP. Our analysis in multiple inherited and de novo patients with CMT1A and HNPP suggests the presence of a precise recurring recombination event as EL mechanism for the generation of uniform duplications and deletions observed in unrelated pedigrees. In one early report describing the 17p11.2-12 duplication associated with CMT1A, the duplication haplotype at the VAW409R3 locus in this de novo patient was heterozygous, suggesting that a meiotic unequal exchange had occurred between parental homologs, not between sister chromatids.

Figure 10:
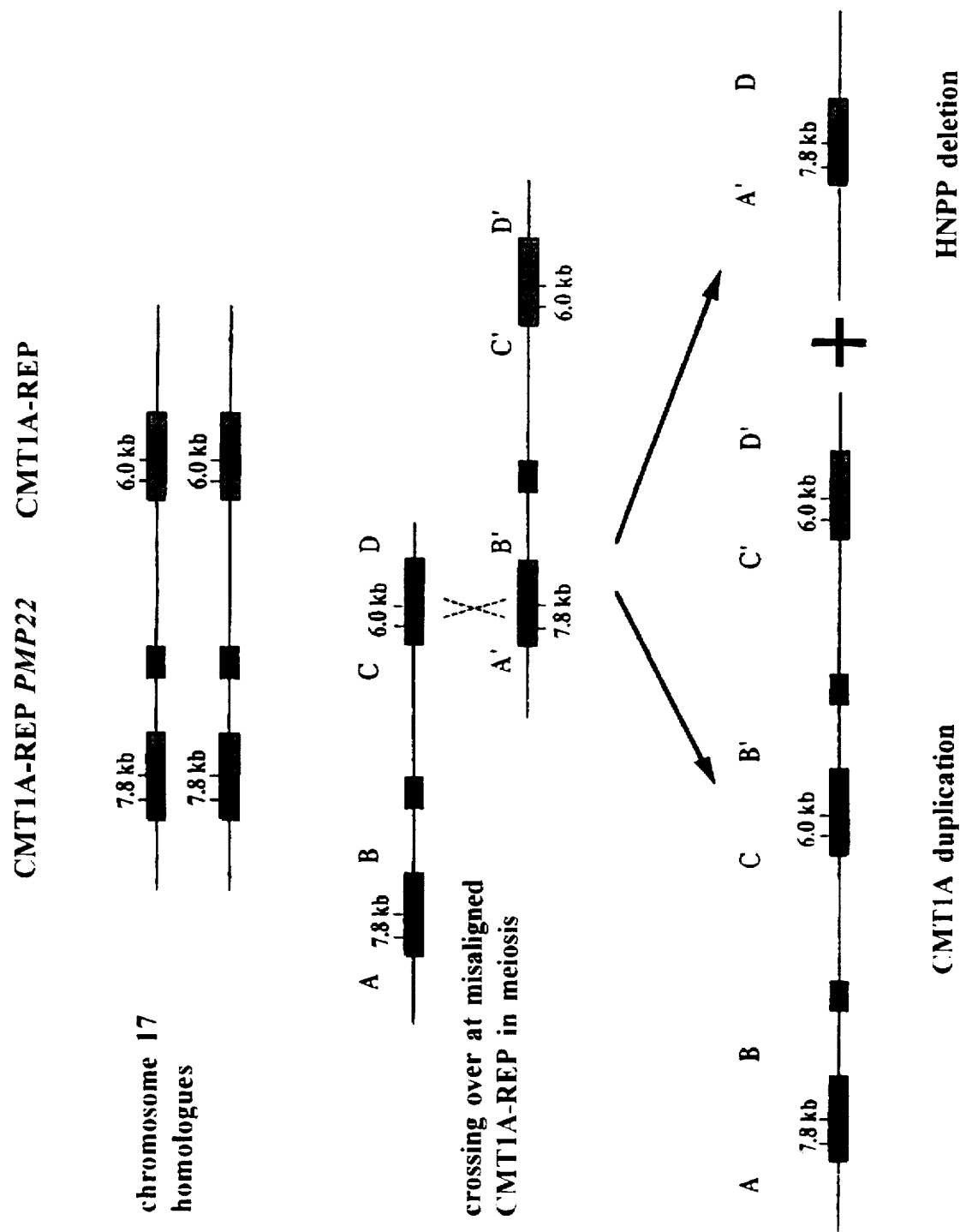
FIG. 10 is a schematic of a model for generation of the CMT1A duplication and the HNPP deletion. Positions of the CMT1A-REP sequences are shown relative to the peripheral myelin protein-22 (PMP-22) gene. Approximate distances are shown in kilobases (kb) and positions of EcoRI fragments detected by probe are shown. Unequal crossover occurs through misalignment mediated by the CMT1A-REP sequences to produce a duplicated and deleted recombinant chromosome.
Figure 11:
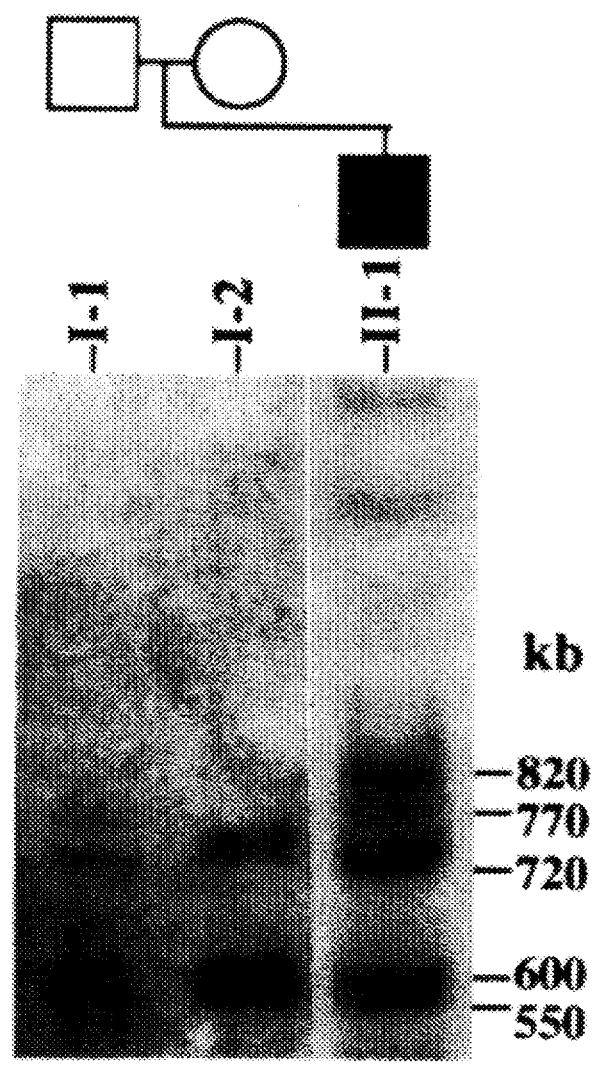
FIG. 11 shows the deletion junction fragments in de novo HNPP.

As the duplication in CMT1A spans an estimated 1.5 Mb, two homologous regions, widely separated within chromosome 17p11.2-12, are apparently required to mediate misalignment during meiotic pairing and a resulting unequal crossover (see FIG. 10). The CMT1A-REP repeat fulfills this hypothesis as it maps to both proximal and distal regions flanking the CMT1A monomer, and is present in three copies of the duplicated CMT1A chromosome.

HNPP is a related peripheral nerve disorder that is associated with a deletion of chromosome 17p11.2-12 and proposed to result from reduced expression of the PMP22 gene. The HNPP deletion appears to be the same size (1.5-Mb) as the region duplicated in CMT1A. Furthermore, the HNPP deletion and CMT1A duplication breakpoints map to the same chromosomal intervals in 17p11.2-12, suggesting that these two disorders are likely the result of reciprocal products from an unequal crossover.

The CMT1A-REP repeat detects two copies of the 6.0-kb EcoRI fragment on the duplicated CMT1A chromosome. As diagrammed in FIG. 10, this observation suggests that in CMT1A the crossover points within both, the proximal and distal CMT1A-REP repeats are distal to the regions containing the 7.8 and 6.0-kb EcoRI fragments. A reciprocally deleted chromosome should retain the 7.8-kb fragment, but lose the 6.0-kb fragment from the distal CMT1A-REP repeat. Loss of the 6.0-kb fragment was detected in two unrelated persons with inherited HNPP, as well as in an individual with a de novo deletion. A reciprocal polarity regarding the locations of the breakpoint to the position is of the CMT1A-REP repeats is present in CMT1A and HNPP. These observations provide further evidence that misalignment of the CMT1A-REP repeat also plays a role in the genesis of the deleted HNPP chromosome and documents the first example of Mendelian syndromes resulting from the reciprocal products of unequal crossover in humans.

While the duplicated chromosome in CMT1A and the deleted chromosome in HNPP are apparently genetic reciprocals, HNPP and CMT1A are both demyelinating neuropathies and therefore do not appear to constitute opposing phenotypes, (syndrome/anti-syndrome or type/counter-type). HNPP and CMT1A appear to result from altered copy number of the PMP22 gene and therefore constitute an unprecedented model of phenotypic consequences resulting from the full range of possible gene dosages in humans.

EXAMPLE 15

Physical Mapping of the HNPP Deletion

To unequivocally demonstrate the presence of the HNPP deletion in HOU44 family members, pulsed field gel electrophoresis (PFGE) followed by Southern hybridization was performed using a probe that maps within the CMT1A-REP repeat flanking the 1.5-Mb CMT1A duplication region. FIG. 13A shows a simplified SacII restriction map of the 17p11.2-p12 region. Physical mapping was previously performed using DNA from a normal individual and a CMT1A duplication patient. The predicted SacII restriction map in the case of the HNPP deletion is indicated (FIG. 13A). Hybridization with the CMT1A-REP probe was predicted to identify dual HNPP deletion junction fragments of approximately 770 kb and 820 kb, due to methylation differences at adjacent SacII sites (FIG. 13A). FIG. 13B shows the results which are consistent with the physical map spanning the 1.5-Mb CMT1A duplication/HNPP deletion region. Individual 117 and her son 732 clearly exhibit dual HNPP deletion junction fragments. The brother of patient 117, individual 735, also exhibits the HNPP deletion junction fragments which are clearly discernible from the other bands normally recognized by the CMT1A-REP probe, and from the 500-kb CMT1A duplication junction fragment (FIG. 13B). Individual 794 also shows the HNPP deletion junction fragments. The asymptomatic individual 788 does not show the HNPP deletion (FIG. 13B). In addition, PFGE analysis was performed on HOU44 extended family members, which showed segregation of the HNPP junction fragments through three generations of HOU44.

Results demonstrating the HNPP deletion in patient 117 were also obtained from the analysis of somatic cell hybrids retaining either the non-deleted or the deleted chromosome 17 homologue. Deletion of markers VAW409 (D17S122), PMP22, VAW412 (D17S125), and EW401 (D17S61) that map within the CMT1A/HNPP region was shown by PCR and Southern analysis of the hybrid retaining the chromosome 17 with the deletion mutation (Hy117-1D), while markers 1516 and VAW411 that map proximal and distal to the CMT1/HNPP region, respectively, were shown to be retained.

EXAMPLE 16

Pulsed Field Gel Electrophoresis

Plugs for pulsed field gel electrophoresis were prepared from whole blood, digested with SacII enzyme, and fractionated on a 1% agarose gel on a CHEF-DRII PFGE apparatus (BioRad). In this preparation the digestion of plugs with restriction enzymes were carried out in 200 μl volume using 20 units of SacII enzyme from IBI, and the pulsed field gel was run for a total of 26 hours (60–90 seconds ramping pulse time) for DNA separation. Southern hybridization of the PFGE nylon filter was performed using the CMT1A-REP probe (7.8 -kb EcoRI fragment) pre-associated with 0.3 mg/ml placental DNA.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and attain the ends and advantages mentioned as well as those inherent therein. The sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the appended claims.

What is claimed is:

1. An isolated DNA molecule consisting of a CMT1A-REP sequence.

2. A method of screening for a deletion or duplication of nucleic acid sequences in a CMT1A region in a sample containing DNA from an individual to be tested, comprising the step of measuring in said sample the presence or absence of a DNA deletion or duplication using a probe that hybridizes to low copy repeat sequences within the CMT1A region, said low copy repeat sequences being close to endpoints of and flanking the CMT1A monomer unit said flanking region designated CMT1A-REP.

3. The method of claim 2, wherein said deletion or duplication is determined by dosage differences measured by Southern blotting analysis.

4. The method of claim 2, where said deletion is determined by detecting specific junction fragments using pulsed field gel electrophoresis.

5. A kit for screening for deletions or duplications in a CMT1A region, comprising a container and a DNA probe which binds to low copy repeat sequences within the CMT1A region, said low copy repeat sequences being close to endpoints of and flanking the CMT1A monomer unit said flanking region designated CMT1A-REP.

6. As a composition of matter, a DNA probe or fragment thereof which binds to a flanking region designated CMT1A-REP sequence, said fragments of sufficient size to distinguish the presence or absence of a duplication or deletion in said flanking region designated CMT1A-REP sequence and be specific for said duplication or deletion.

7. A method of screening for a deletion at the CMT1A locus, wherein said deletion is determined by detecting specific junction fragments, comprising a CMT1A-REP sequence using pulsed field gel electrophoresis, saidjunction fragments of sufficient size to distinguish the presence or absence of the deletion and be specific for the deletion.

* * * * *